United States Patent [19]
Betush

[11] 4,117,861
[45] Oct. 3, 1978

[54] CONTROL AND SELECTOR UNIT FOR DENTAL HANDPIECES

[75] Inventor: Frank A. Betush, Santa Monica, Calif.

[73] Assignee: Progressive Machine Products, Inc., Los Angeles, Calif.

[21] Appl. No.: 791,711

[22] Filed: Apr. 28, 1977

[51] Int. Cl.² ............................................. F16K 7/07
[52] U.S. Cl. ...................................... 137/595; 32/22; 251/5; 251/9
[58] Field of Search .................... 32/22; 251/5, 9, 10; 137/595

[56] References Cited

U.S. PATENT DOCUMENTS

| | | | |
|---|---|---|---|
| 2,734,526 | 2/1956 | Aagaard | 251/5 X |
| 2,895,653 | 7/1959 | Giepen | 251/9 X |
| 3,316,935 | 5/1967 | Kaiser | 137/595 |
| 3,584,830 | 6/1971 | Koehn | 251/10 X |

FOREIGN PATENT DOCUMENTS

| | | | |
|---|---|---|---|
| 2,341,309 | 2/1975 | Fed. Rep. of Germany | 251/9 |
| 585,867 | 3/1977 | Switzerland | 251/9 |

*Primary Examiner*—Robert G. Nilson
*Attorney, Agent, or Firm*—Keith D. Beecher

[57] ABSTRACT

A control and selector unit for a dental handpiece is provided of the high pressure air driven type. The control and selector unit includes a bracket for supporting a handpiece, and a resilient metal strip having a free end extending into the bracket. The other end of the resilient strip is supported on the base of the control unit, and the strip acts as a pinch valve for a tube carrying high pressure drive air to the handpiece. The pinch valve releases the tube when the handpiece is removed from the bracket so as to cause the handpiece to be activated. The control unit may also include additional resilient strip pinch valve controls for controlling the supply of coolant air, or other gases, and water to the handpiece when the handpiece is removed from the bracket. A swell tube may be included in the control unit to provide a delayed action for the latter pinch valve resilient strip controls, so that the coolant air, or other gases, and water may be supplied to the handpiece only after the handpiece has been brought up to speed by the drive air. The water control may also include a "suck-back" feature which prevents dripping when the handpiece is returned to the bracket at the end of a dental operation.

7 Claims, 2 Drawing Figures

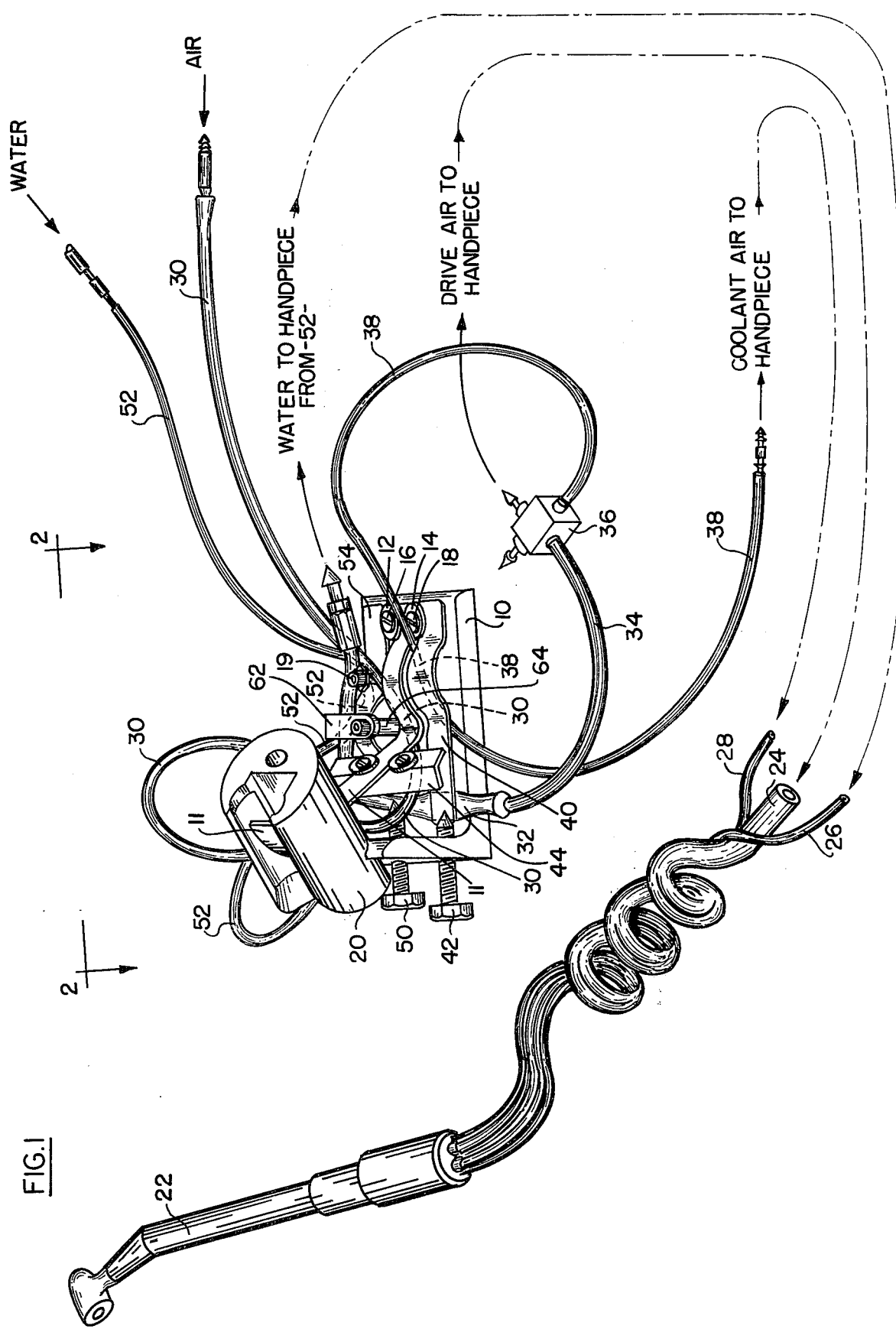

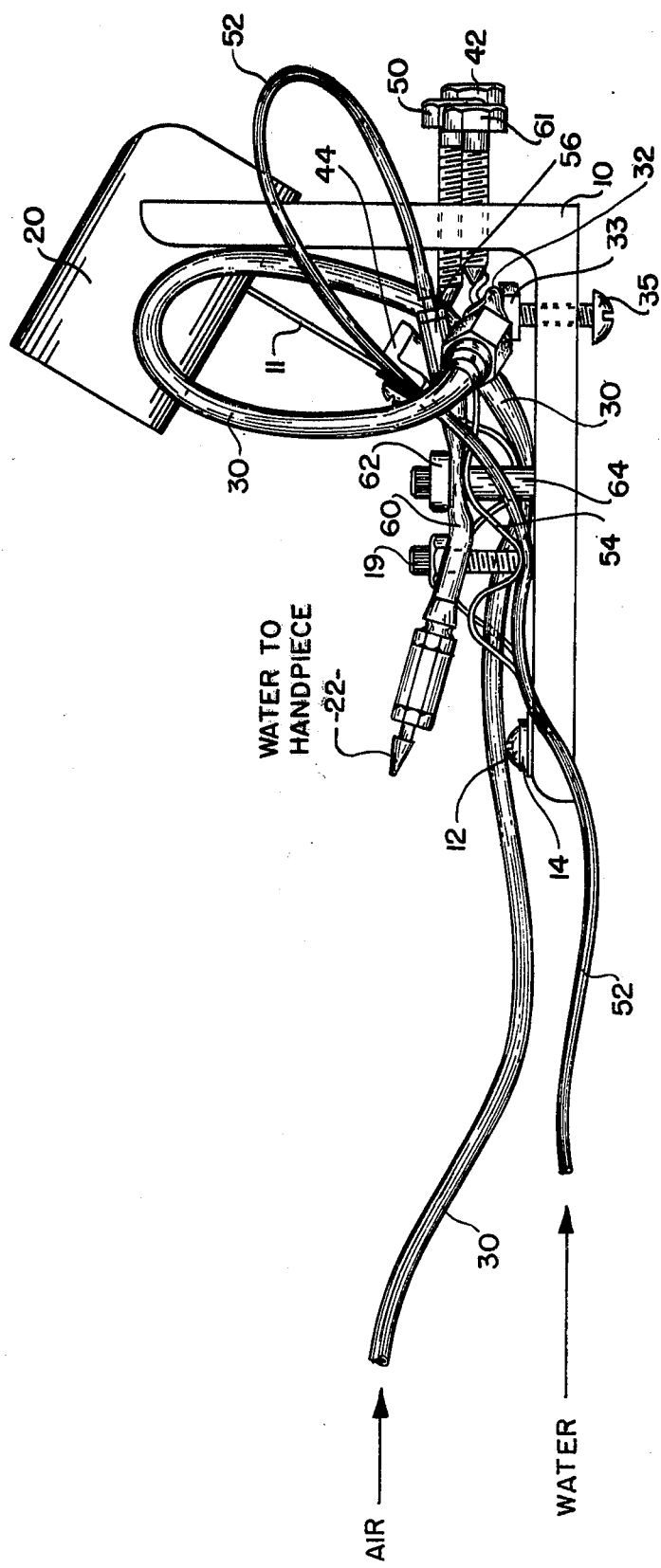

CONTROL AND SELECTOR UNIT FOR DENTAL HANDPIECES

BACKGROUND OF THE INVENTION

It is the usual practice in present-day dental offices to use a number of separate handpieces which are driven at high speeds by compressed air. In many instances, the high speed air driven instruments also emit a spray of water with the drive air as a coolant; and it may also be controlled to emit pressurized air for cooling purposes, or other gases. It is the common practice in the prior art for such handpieces to be supported on individual brackets which, in turn, are mounted on a console adjacent to the dental chair. Compressed air and pressurized water are supplied to the various handpieces in the prior art equipment through individual tubes. The air and water are obtained from the usual mains, and the flow thereof to the console is usually controlled by foot-operated valves. In the prior art, additional valves are provided in the console so that the flow of the pressurized air and water to the individual handpieces may also be controlled. With such prior art equipment, the dentist causes the air and water to be supplied to the console by actuating his foot-operated valves; and he then causes the air or water, or both, to be supplied to a selected handpiece, by actuating appropriate valves in the console.

The valves in the prior art consoles, in addition to being complex and expensive, are difficult to operate, and they often require both hands of the dentist to control them. The control unit of the present invention, on the other hand, provides an improved valve assembly for distributing the pressurized air and water to the various dental handpieces associated with the console, and this is achieved in such a manner that the selected handpiece may be activated, as it is selected by the dentist. It will also become evident as the present description proceeds that although the pinch valve control unit of the present invention is described in conjunction with a dental handpiece, it has wider application in the art wherever the flow of fluid through a supply tube is to be controlled.

U.S. Pat. No. 3,755,899 which issued Sept. 4, 1973 to the present inventor describes apparatus in which each dental handpiece is supported in a holder on a pivotally mounted arm, and each arm includes a pinch block at one end which pinches a corresponding flexible tube to prevent the flow of fluid to the handpiece when the holder is in its down position, but which permits the flow of fluid through the tube to the selected handpiece when the holder is in its up position. Therefore, in using the apparatus described in the patent, the dentist first selects a particular handpiece from its holder, and he then flips the holder to its up position so as to activate the handpiece.

The control unit of the present invention has certain advantages over the control unit described in the prior patent referred to above in that it is less expensive to construct, and in that it operates by the insertion and withdrawal of the handpiece from the bracket and there is no need to tilt the bracket. Also, the control unit of the present invention is capable of performing certain functions beyond the capabilities of the control unit of the aforesaid patent, as will be described.

The control unit of the invention is reliable in operaton, and it is not subject to excessive wear. Whenever a tube controlled by the unit shows any evidence of wear, it is merely necessary to shift the tube so that a new portion thereof is pinched by the unit. The unit of the invention also provides a complete separation of the air and water controls which enhances its reliability. The unit of the invention is also advantageous in that it is flexible, and can be constructed to perform more or less multiple functions depending upon the particular installation.

As will be described in detail herein, the control unit of the invention makes use of resilient metal strips which, for example, may be formed of beryllium, and which act as pinch valves. Swell tubes are also used in the unit in certain of its embodiments, as will be described, to provide a delayed actuation of certain of the resilient strip pinch valves. For example, the control unit may provide for the introduction of water or coolant air to the handpiece only after the handpiece has come up to speed, and this function is controlled by the swell tube. As mentioned above, the control unit may also incorporate a "suck-back" function in the water line to prevent dripping after the handpiece has been replaced in the bracket.

BRIEF DESCRIPTION OF THE DRAWINGS

FIG. 1 is a perspective view of a control unit constructed in accordance with one embodiment of the invention; and FIG. 2 is a side view taken from one side of the unit along the lines 2—2 of FIG. 1.

DETAILED DESCRIPTION OF THE ILLUSTRATED EMBODIMENT

The control unit shown in FIGS. 1 and 2 is shown inverted in order to reveal the operating components on the underside of its base 10. A first resilient metal strip 11, formed of beryllium, or other appropriate material, has one end supported on base 10 by washers 12 and 14 which, in turn, are attached to the base by screws 16 and 18. The washers may be eccentrically mounted on the base to permit them to be turned so as to adjust the pressure exerted on strip 11. A screw 19 is threaded into base 10 and is adjustable to limit the travel of strip 11 away from base 10.

A bracket 20 is mounted on base 10, and it is shaped to receive the handpiece 22. Handpiece 22 is an air driven type. High pressure drive air is supplied to the handpiece through a flexible tube 24; coolant air, or other gases, are supplied to the handpiece through a flexible tube 28; and water is supplied to the handpiece through a flexible tube 26.

Compressed air from an appropriate foot control, or other source, is supplied to the control unit through a flexible tube 30. Tube 30 passes between a bend in the resilient strip 11 and the base to be pinched against the base when the handpiece is inserted into the bracket 20. For this purpose, the distal free end of the resilient strip 11 extends into the bracket, to be engaged by the handpiece, when the handpiece is inserted into the bracket.

The ends of tube 30 is coupled to a swell tube 32 which, in turn, is coupled to a tube 34, the latter tube being connected to the handpiece air tube 24 through a fitting 36. A plate 33 (FIG. 2) is interposed between the swell tube 32 and base 10. Plate 33 may be moved against the swell tube by a screw 35 to adjust the operational effect of the swell tube.

When the foot control or other air source is activated, drive air is automatically supplied to handpiece 22 when it is removed from the bracket 20, and without the need for any other operation on the part of the dentist. The amount of drive air supplied to the handpiece may be controlled by adjusting screw 19 which controls the air flow through tube 30.

Tube 34 is also coupled through fitting 36 to a further flexible tube 38. Tube 38 passes between a bend in a further resilient metal strip 40 and the base 10, and is then connected to the coolant air tube 28 of the handpiece. One end of resilient strip 40 is mounted on base 10 adjacent to strip 11 by the washer 14 and screw 18. The distal free end of strip 40 may be engaged by the end of a screw 42, so that the strip may be independently operated to its down position to pinch off tube 38 by turning the screw 42 to its inner position. Screw 42 may be operated by the dentist to control the flow of coolant air to the handpiece, or to shut off the coolant air, when coolant air, or other gas, is not required at the handpiece. Screw 42 may be replaced by a toggle, or other appropriate manually operated actuator, or solenoid controlled actuator, if so desired.

Swell tube 32 passes between the free end of strip 40 and plate 33, and if the strip is not set manually to its pinch position by screw 42, the swell tube will lift the strip to release the tube 38 and permit coolant air or other gas to flow to the handpiece, after sufficient air pressure has built up in the swell tube, thereby providing the desired delay in the flow of the coolant air to the handpiece, permitting the handpiece to come up to speed before the coolant air is introduced, thereto. The amount of this delay may be adjusted, for example, by adjusting the screw 35 which, in turn, moves plate 33 towards or away from the swell tube.

A tie bar 44 is attached to strip 11 by screws 46 and 48, and the tie bar forces strip 40 to its pinch position to pinch off the air through tube 38 whenever the handpiece is inserted into bracket 20. Therefore, strip 40 is conditioned for operation by swell tube 32 only when the handpiece is removed from bracket 20. A further screw 50 is threaded through base 10 and engages the tie bar 44 to hold the strips 11 and 40 in their pinch position even when the handpiece has been removed from the bracket 20. The tie bar serves as a safety lock and permits drill changes, cleaning and other operations as to be made by an assistant on the particular handpiece without activating the handpiece, while the dentist is activating another handpiece. Screw 50, likewise, may be replaced by a toggle, or other appropriate manual or solenoid control, if so desired.

Water is supplied to the handpiece from the usual mains, or from a pressurized plastic water canister, through a flexible tube 52. Tube 52 passes between a bend in a third resilient metal strip 54 and base 10 to cause it to be pinched against base 10 by the strip. One end of strip 54 is mounted to the base 10 by washer 12 of screw 16. Swell tube 32 also passes under the free end of strip 54 to cause the water to flow to the handpiece through fitting 56 (which is attached to the handpiece water tube 26) when the swell tube becomes inflated either by the drive air supplied to the handpiece, or by air from other remote air sources should water flow be required without operating the handpiece.

Tube 52 is coupled through fitting 56 through a further tube 60. The further tube 60 passes between a second bend in strip 54 (FIG. 2) and a rigid arm 62. Arm 62 is mounted on an eccentric post 64 which, in turn, is supported on base 10. Upon the actuation of a foot control, or other remote air source, strip 54 is moved by the swell tube 32 to open tube 52, after which tube 60 is partially pinched against arm 62 to restrict the volume of water contained in tube 60 to some extent. However, as air pressure begins to exhaust from the swell tube 32, the swell tube moves strip 54 to a position in which the strip pinches tube 52 and begins to release tube 60. This action of the strip cuts off the flow of water through tube 52, then it also creates a volume increase and suction pressure in tube 60, so as to cause tube 60 to suck back any water in the handpiece 22 so as to prevent dripping. The air pressure in swell tube 32 is fully released at this time by exhausting back through tube 30 as the foot control, or other remote air source, is reactivated. The amount of suck back may be adjusted by rotating the eccentric post 64 to move arm 62 nearer to or further from strip 54.

A screw 61 is threaded through base 10 to engage the free end of strip 54. The screw may be adjusted to limit the movement of strip 54 away from base 10 partially to pinch off tube 52, and cut off, or restrict, the maximum supply volume of water to the handpiece. Screw 62 may, likewise, be replaced by a toggle, or other manual or electrically energized actuator, if so desired. Strip 54 is also conditioned for operation by swell tube 32, but only when handpiece 22 is removed from bracket 20, and when screw 50 does not engage tie bar 44.

It will be appreciated that while a particular embodiment of the control unit of the invention has been shown and described, modifications may be made. It is intended in the claims to cover all modifications which come within the true spirit and scope of the invention.

What is claimed is:

1. A control unit for controlling the flow of a pressurized fluid comprising: a base; a first resilient strip having one end affixed to said base and having a free end displaced from said base; an actuator mounted on the free end of said first resilient strip in position to move the free end of said first resilient strip between a first position and a second position; a first flexible tube for supplying pressurized fluid from a source to a utilization means positioned to be engaged by a portion of said first resilient strip to be pinched thereby to a closed condition when the free end of said first resilient strip is moved from said first position towards said second position; a second resilient strip mounted on said base adjacent to said first resilient strip and having one end affixed to said base and a free end displaced from said base; coupling means extending between the first and second resilient strips to cause the second resilient strip to be maintained in a second position when the first resilient strip is in its second position; and a second flexible tube for supplying pressurized fluid to the utilization means positioned to be engaged by a portion of said second strip to be pinched thereby to a closed condition when said second strip is in its second position.

2. The control unit defined in claim 1, and which includes a swell tube mounted between said base and said free end of said second resilient strip to move said second resilient strip from said second position towards a first position as said swell tube is inflated.

3. The control unit defined in claim 2, in which said swell tube is interposed in said first flexible tube to be inflated when the first resilient strip moves to its first position to cause the first flexible tube to be opened.

4. The control unit defined in claim 1, and which includes a manually-controlled means mounted on said base in position to engage the free end of said second resilient strip to maintain the second strip in its second position independent of the actuator so as to provide an independent operator for said second strip.

5. The control unit defined in claim 1, in which said second flexible tube is further engaged by a second portion of said second resilient strip to be partially pinched thereby when the free end of said second resilient strip is in said first position and to be released when the free end of said second resilient strip is moved to said second position so as to create a suck-back effect in said second tube.

6. A control unit for controlling the flow of a pressurized fluid comprising: a base; a resilient strip having one end affixed to said base and having a free end displaced from said base; and a flexible tube for supplying pressurized fluid from a source to a utilization means positioned to be engaged by a portion of said resilient strip to be pinched thereby to a closed condition when the free end of said strip is moved toward said base from a first position towards a second position; said flexible tube being positioned also to be engaged by a further portion of said resilient strip to be pinched thereby to a partially closed condition when said free end of said strip is moved away from said base from said second position towards said first position, and to be released when the free end of said strip is moved towards said base from said first position towards said second position to create a suck-back effect in said tube.

7. The control unit defined in claim 6, and which includes an actuator mounted on said base in position to move the free end of said strip between said first position and said second position.

* * * * *